(12) United States Patent
Meade et al.

(10) Patent No.: US 11,484,916 B2
(45) Date of Patent: *Nov. 1, 2022

(54) HIGH-PRESSURE WATER DEBRIDEMENT SYSTEM

(71) Applicant: ALLOSOURCE, Centennial, CO (US)

(72) Inventors: Denis M. Meade, Littleton, CO (US); Shane Graham, Parker, CO (US); Kyle von Kaenel, Thornton, CO (US)

(73) Assignee: Allosource, Centennial, CO (US)

( * ) Notice: Subject to any disclaimer, the term of this patent is extended or adjusted under 35 U.S.C. 154(b) by 302 days.

This patent is subject to a terminal disclaimer.

(21) Appl. No.: 16/838,318

(22) Filed: Apr. 2, 2020

(65) Prior Publication Data
US 2020/0230657 A1 Jul. 23, 2020

Related U.S. Application Data

(62) Division of application No. 15/815,075, filed on Nov. 16, 2017, now Pat. No. 10,661,312.
(Continued)

(51) Int. Cl.
*B08B 3/02* (2006.01)
*A61F 2/46* (2006.01)
(Continued)

(52) U.S. Cl.
CPC .............. *B08B 3/02* (2013.01); *A61B 90/70* (2016.02); *A61F 2/4644* (2013.01); *A61F 2002/4646* (2013.01); *A61L 2/0011* (2013.01)

(58) Field of Classification Search
CPC ............ A61B 90/70; A61F 2002/4646; A61F 2/4644; B44D 3/006; B08B 3/02; B08B 3/022
See application file for complete search history.

(56) References Cited

U.S. PATENT DOCUMENTS

| 4,130,443 A | 12/1978 | Dulin |
| 5,038,809 A | 8/1991 | Rodgers et al. |

(Continued)

FOREIGN PATENT DOCUMENTS

| EP | 1 955 815 A1 | 8/2008 |
| WO | 1998/041245 A1 | 9/1998 |
| WO | 2010/008453 A2 | 1/2010 |

OTHER PUBLICATIONS

European Search Report for EP 18152227.7 dated Mar. 7, 2018, 8 pp.
(Continued)

*Primary Examiner* — Joseph L. Perrin
*Assistant Examiner* — Kevin G Lee
(74) *Attorney, Agent, or Firm* — James A. Sheridan; Sheridan Law, LLC

(57) ABSTRACT

There is disclosed a system and methods for debriding soft tissue from bone using a high-pressure water debridement system. One embodiment includes a cylindrical sleeve bounded by endcaps and having a drainage port positioned for effluent drainage. A central shaft is configured to receive a bone segment and is disposed along a longitudinal center of the sleeve and rotatively coupled between the endcaps. At least one high-pressure water nozzle is disposed on each side of the sleeve, each of which is positioned to impact the bone segment with a high-pressure water stream. A rotational actuator is configured to rotate the central shaft and the bone segment relative to the sleeve and the water nozzles such that when the high-pressure water nozzles are operational, the high-pressure water streams debride the bone segment. Other embodiments are also disclosed.

20 Claims, 8 Drawing Sheets

Related U.S. Application Data

(60) Provisional application No. 62/449,408, filed on Jan. 23, 2017.

(51) Int. Cl.
  *A61B 90/70* (2016.01)
  *A61L 2/00* (2006.01)

(56) References Cited

U.S. PATENT DOCUMENTS

| | | | |
|---|---|---|---|
| 5,333,626 A | 8/1994 | Morse et al. | |
| 5,614,031 A | 3/1997 | Cushing | |
| 5,846,484 A * | 12/1998 | Scarborough | A61L 27/3683 422/295 |
| 6,038,787 A | 3/2000 | Dean et al. | |
| 2001/0047818 A1 | 12/2001 | Bastien | |
| 2002/0081959 A1 | 6/2002 | Benedict et al. | |
| 2002/0166578 A1 | 11/2002 | Leblond | |
| 2009/0314314 A1 | 12/2009 | Klein et al. | |
| 2012/0080118 A1 | 4/2012 | Klein | |
| 2014/0166058 A1 | 6/2014 | Klein et al. | |
| 2014/0263778 A1 | 9/2014 | Koltz et al. | |

OTHER PUBLICATIONS

Precise Excision, VersaJet II Hydrosurgery System, Smith & Nephew, Inc., 2013, 6 pp.

VersaJet Hydrosurgery System, Smith & Nephew, Inc. 2004, 4 pp.

VersaJet II, Hydrosurgery System, http://www.smith-nephew.com/key-products/advanced-wound-management/versajet/, accessed Dec. 13, 2017, 3 pp.

VersaJet: Method of Action, https://www.youtube.com/watch?v=pmG27jxA-Fo, accessed on Dec. 13, 2017, Smith & Nephew, Inc., 1 pp.

Brown, Ashley, "A Device for Debridement Using High Pressure Water Jets", Thesis, S.M. Massachusetts Institute of Technology, Dept. of Mechanical Engineering, 2014, https://dspace.mit.edu/handle/1721.1/92223, 3 pp.

* cited by examiner

HIGH-PRESSURE WATER DEBRIDEMENT SYSTEM

REFERENCE TO PENDING PRIOR PATENT APPLICATION

This application is a divisional of U.S. patent application Ser. No. 15/815,075, filed Nov. 16, 2017 by Denis M. Meade, Shane Graham, and Kyle von Kaenel, for HIGH-PRESSURE WATER DEBRIDEMENT SYSTEM, which claims the benefit under 35 U.S.C. 119 (e) of U.S. Provisional Patent Application No. 62/449,408, filed Jan. 23, 2017 by Denis M. Meade, Shane Graham, and Kyle von Kaenel for "HIGH PRESSURE WATER DEBRIDEMENT SYSTEM," all of which patent applications are is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from cadaveric donor-derived, living-related, or living-unrelated donors and can help patients regain mobility, restore function, enjoy a better quality of life, and even save lives in the case of cardiovascular tissue or skin.

Currently, soft tissue debridement from donated, cadaveric human bone is a manually intensive procedure that requires operators/technicians to manipulate metal gouges to repeatedly scrape extraneous adherent soft tissue (e.g., muscle and other non-osseous tissue) from the bone. This process is time consuming. A time-motion study assessing the amount of time required to manually debride human tissue from bone, excluding set-up time, revealed that the mean time to manually debride a human femur is nine minutes, while the mean time to debride a human tibia is seven minutes. The existing process also requires the use of sharp objects, while simultaneously gripping a slippery surface (i.e., bone and soft tissue) and requires operators to make multiple, repetitive hand-arm movements to remove all unnecessary tissue. These repetitive motions can lead to hand-arm related injuries and increase the operator's risk of musculoskeletal disorders resulting from repetitive motion damage, including tendonitis, carpal tunnel syndrome, osteoarthritis, and other pathologies. Such injuries and disorders can affect the mission, bottom line, work productivity, and employee satisfaction and engagement of an allograft processing center or tissue bank.

Others have attempted to provide automated or semi-automated systems and tools for tissue debridement from bone, but these systems present time, safety, sterilization, effluent disposal, and efficiency challenges.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a high-pressure water debridement system for removing soft tissue from a bone segment. The system may include (1) an outer sleeve defining a longitudinal center axis, the outer sleeve having an interior bounded by first and second endcaps; (2) a central shaft disposed along the longitudinal center axis of the outer sleeve and rotatively coupled between the first and the second endcaps, the central shaft configured to receive the bone segment; and (3) one or more high-pressure water nozzles disposed on each side of the outer sleeve. Each of the high-pressure water nozzles may be positioned to impact the bone segment with a high-pressure water stream, wherein when the high-pressure water nozzles are activated and when an actuating force rotates the central shaft relative to the outer sleeve, the bone segment rotates relative to the outer sleeve and oscillates linearly along the longitudinal center axis within a spray zone of the high-pressure water nozzles such that the high-pressure water streams debride the bone segment.

Another embodiment provides a system for soft tissue debridement of a bone segment. The system may include (1) a cylindrical sleeve having an interior bounded by first and second endcaps, the cylindrical sleeve having a drainage port positioned for effluent drainage; (2) a central shaft configured to receive a bone segment, the central shaft disposed along a longitudinal center of the cylindrical sleeve and rotatively coupled between the first and the second endcaps; (3) at least one high-pressure water nozzle disposed on each side of the cylindrical sleeve, each of the high-pressure water nozzles positioned to impact the bone segment with a high-pressure water stream; and (4) a rotational actuator configured to rotate the central shaft and the bone segment relative to the cylindrical sleeve and the high-pressure water nozzles such that when the high-pressure water nozzles are operational, the high-pressure water streams debride the bone segment.

Yet another embodiment provides a method of debriding soft tissue from a cadaveric bone segment using a high-pressure water debridement system including an outer sleeve defining a longitudinal axis and having an interior bounded by an outer wall and first and second endcaps, a central shaft disposed along the longitudinal axis and rotatively coupled between the first and the second endcaps, and a number of high-pressure water nozzles disposed within the outer wall of the outer sleeve. The method may include the steps of (1) affixing the bone segment about the central shaft such that the bone segment is positioned within a spray zone bounded by a first positive stop and a second positive stop; (2) disposing the outer sleeve about the bone segment and the first and the second positive stops such that a first end of the central shaft protrudes from the first endcap and a second end of the central shaft protrudes from the second endcap; (3) rotating the central shaft relative to the first and the second endcaps such that the bone segment rotates relative to the outer sleeve and oscillates linearly along the longitudinal axis within the spray zone; and (4) activating the number of the high-pressure water nozzles such that each of the high-pressure water nozzles directs a high-pressure water stream into the spray zone to debride the bone segment.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
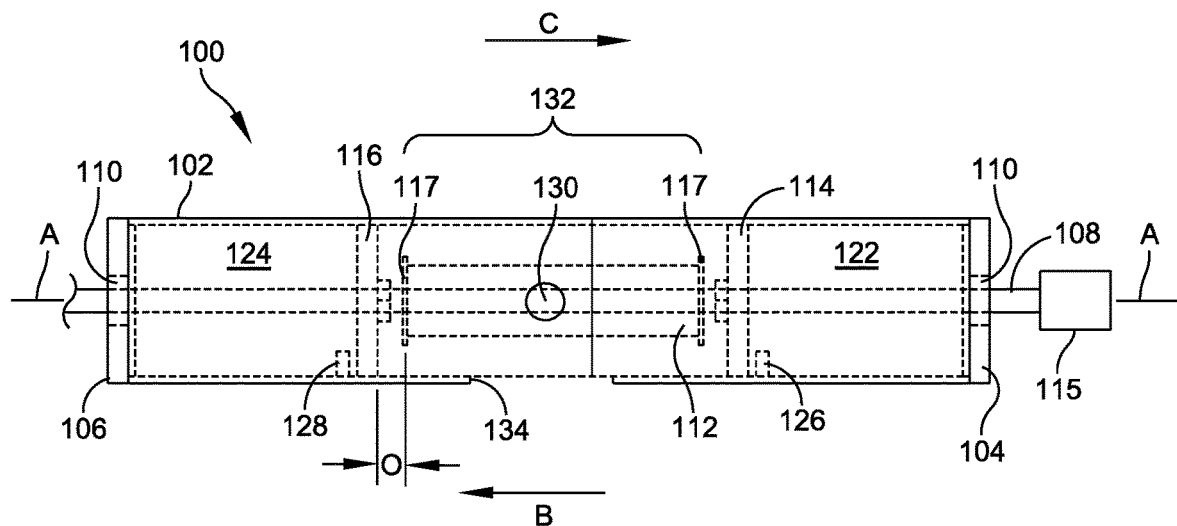
FIG. 1 illustrates a side view of one embodiment of a high-pressure water debridement system for debriding soft tissue from bone.
Figure 2:
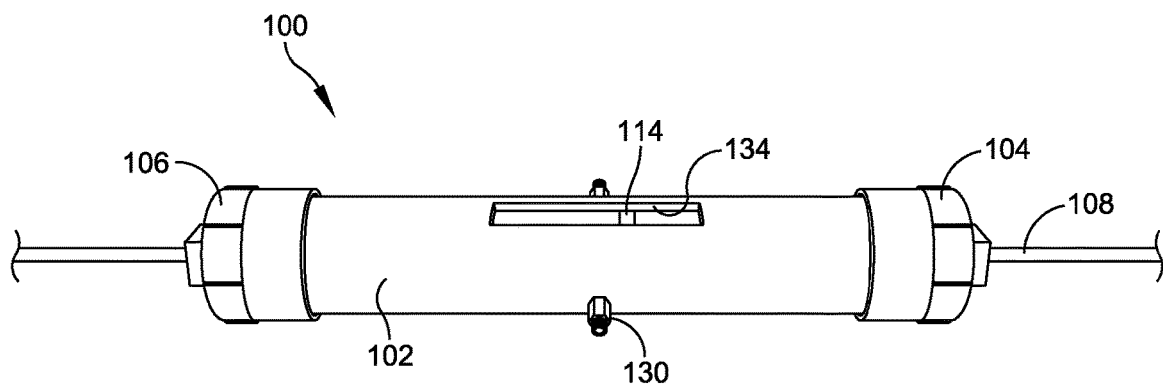
FIG. 2 illustrates a bottom perspective view of the system of FIG. 1.
Figure 3:
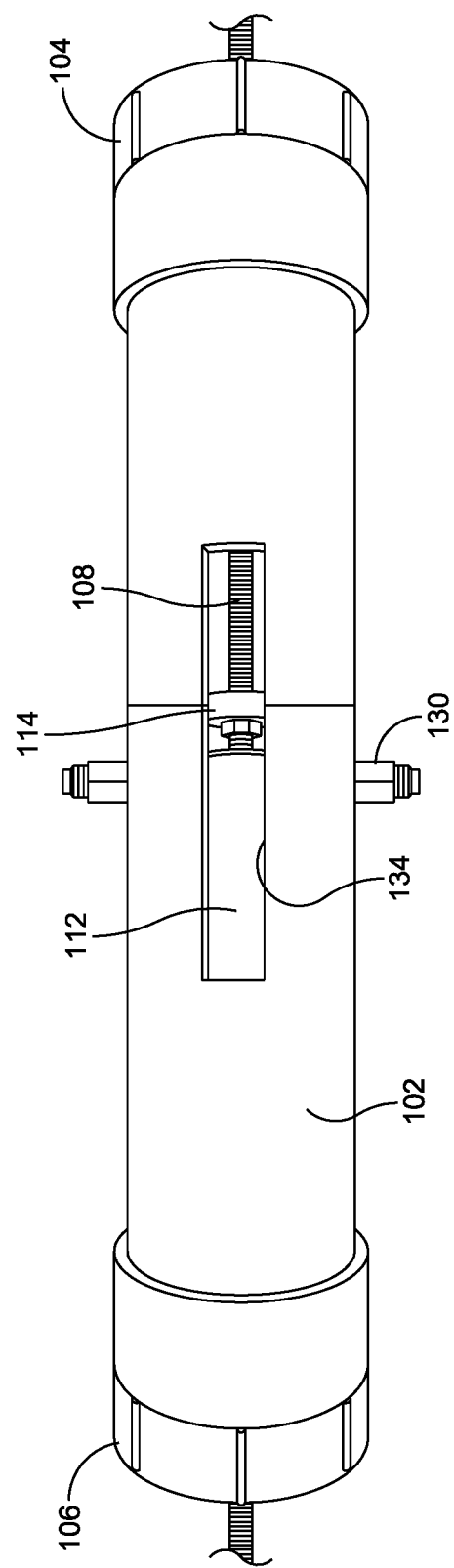
FIG. 3 illustrates a bottom view of the system of FIG. 1.
Figure 4:
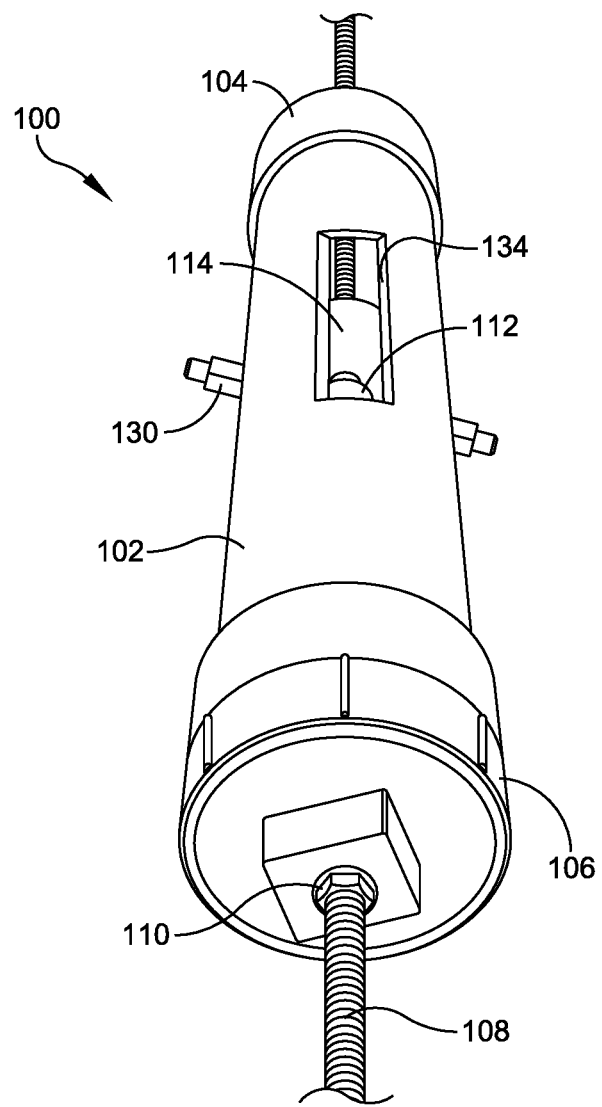
FIG. 4 illustrates a front perspective view of the system of FIG. 1.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to soft tissue debridement using a contained, automated system that leverages pressurized water emanating from multiple high-pressure water jet nozzles to remove soft tissue from donated, cadaveric bone. The system automates the soft tissue debriding process, thereby significantly reducing and/or eliminating the need for manual tissue removal and for manual actuation of a debridement system. Effluent from the system may be passed into a properly designated waste container or disposal system for disposal.

Embodiments of the system rapidly debride extraneous soft tissues in a manner that is safe, contained, and that does not require either manual tissue removal or manual system actuation. One embodiment provides a high-pressure water debridement system that includes an enclosed cylindrical sleeve, or "bone tube," through which a central shaft is passed. A bone segment with tissue disposed thereon may be placed about the central shaft such that the shaft intersects the bone segment within the bone tube. One or more high-pressure water nozzles may be located on either side of an outer circumference of the bone tube, such that when the central rod is rotated within the bone tube, either using an external rotational actuator or rotational actuation imparted by the high-pressure water impinging upon the bone segment itself, the resulting hydro impact effectively debrides the bone. The bone tube may include a drainage port formed within a wall of the bone tube and positioned beneath the bone segment when undergoing debridement. Thus, effluent from the system may be passed through the port hole and captured for efficient disposal.

FIGS. 1-4 illustrate various side, perspective, and bottom views of one embodiment of a high-pressure water debridement system 100 for debriding soft tissue from a bone segment. In this embodiment, the system 100 may include a cylindrical sleeve 102 bounded by first and second endcaps 104, 106, respectively. A central shaft 108 may pass through a longitudinal center of the sleeve 102 along a longitudinal shaft axis A. The central shaft 108 may be rotatively coupled with the first and the second endcaps 104, 106 in any appropriate manner. In one embodiment, the shaft 108 may be a threaded shaft that threadably engages with a nut 110 disposed within each of the first and second endcaps 104, 106. The nuts 110 may be affixed within each of the first and the second endcaps 104, 106 using any appropriate attachment method or mechanism, including a press fit or an adhesive.

Figure 5:
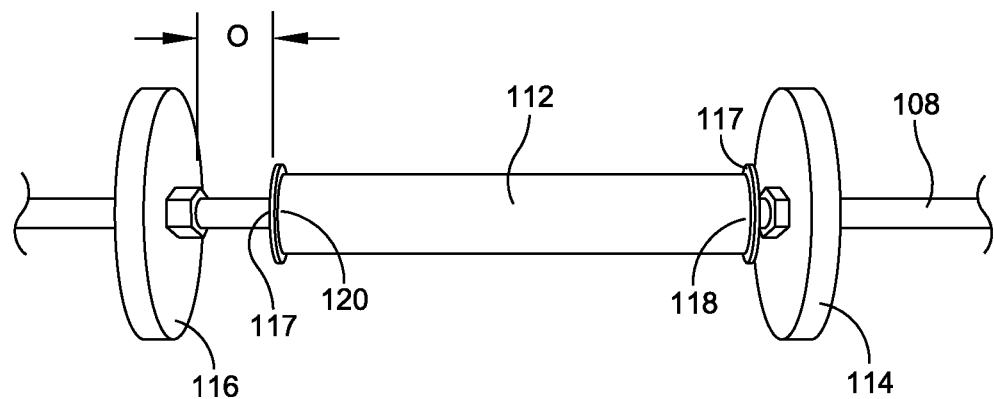
FIG. 5 illustrates one embodiment of a central shaft and first and second positive stops of the high-pressure water debridement system of FIGS. 1-4, as disposed in relation to a bone segment for debridement.

FIG. 5 illustrates a perspective view of a bone segment 112 mounted upon the central shaft 108, for ultimate placement within the sleeve 102, as discussed above and shown in FIGS. 1-4. In this embodiment, first and second positive or hard stops 114, 116 may be disposed along the central shaft 108 (e.g., with a slip fit about the shaft), one at each end of first and second respective ends 118, 120 of the bone segment 112 disposed upon the shaft 108 for debridement. An offset, O, may separate the second end 120 of the bone segment 112 from the second positive stop 116, creating a space within which the bone segment 112 may travel linearly between the first and second positive stops 114, 116 during water debridement. In one embodiment, each end 118, 120 of the bone segment 112 may be fitted with a cap 117 that attaches directly to the bone 112 and the shaft 108. The caps 117 may serve to affix the bone segment 112 relative to the shaft 108 and to facilitate smooth, low-friction interaction between the first and the second ends 118, 120 of the bone segment and the hard stops 114, 116 as the shaft 108, and thus the bone 112, translates back and forth, or oscillates, between the first and the second positive stops 114, 116 during debridement.

To maintain the positioning the positive stops 114, 116 relative to the sleeve 102 when the system 100 is assembled, the first and the second positive stops 114, 116 may be bounded in an outward direction toward the endcaps 104, 106 in any appropriate manner. For example, and in one embodiment, the cylindrical sleeve 102 may be formed of first and second respective mating halves 122, 124 that engage/connect in the middle to envelop the hard stops 114, 116 and the bone segment 112 disposed therebetween. To limit travel of the bone segment 112 and the positive stops 114, 116, each respective half 122, 124 of the sleeve 102 may incorporate a built-in travel limit 126, 128 (FIG. 1) such as, for example, a protrusion, ring, or another physical barrier configured to bound the respective positive stop 114, 116 in the outward direction when the sleeve 102 is assembled about the shaft 108, the bone segment 112, and the positive stops 114, 116. In another embodiment, the positive stops 114, 116 may be held in position relative to the sleeve 102 via a frictional fit.

In one embodiment, one or more high-pressure water nozzles 130 may be located on each side of an outer perimeter of the cylindrical sleeve 102. The nozzles 130 may be positioned such that when activated, a high-pressure water stream is directed toward the bone segment 112 within the sleeve 102. The nozzles 130 may be connected in any appropriate manner with a water and air manifold system (not shown) available within a typical allograft processing room, thereby permitting users to regulate water pressure as necessary. In one embodiment, the nozzles 130 may be connected with the water system via a commercially available quick-disconnect connector or connectors.

During operation, an external actuator 115 such as, for example, a drill or an electric motor may be coupled with the central shaft 108 to drive rotational motion of the shaft 108 relative to the stationary cylindrical sleeve 102. In one embodiment shown in FIG. 1, when the external actuator 115 is actuated to rotate the shaft 108 in a first rotational direction relative to the nuts 110 disposed within the first and the second endcaps 104, 106, the shaft 108, and thus the bone segment 112 disposed thereon, rotates in the first rotational direction and simultaneously travels in a first linear direction away from the first positive stop 114, toward the second positive stop 116, and through the offset, O, as denoted by arrow B. When the direction of shaft rotation is reversed, the shaft 108 and the bone segment 112 also reverse linear direction and travel in a second linear direction away from the second positive stop 116, toward the first positive stop 114, and back through the offset, O, as denoted by arrow C. Thus, the rotational motion provided by the external actuator 115 both rotates the bone segment 112 and oscillates the bone segment 112 linearly within a spray zone 132 of the high-pressure streams provided by the nozzles 130. The resulting hydro impact effectively debrides the bone segment 112 in a manner of seconds (i.e., less than 60 seconds), while eliminating the need for manual tissue removal and for manual actuation (e.g., rotation and/or translation) of the shaft 108, the bone segment 112, or any other components of the system 100.

Figure 6:
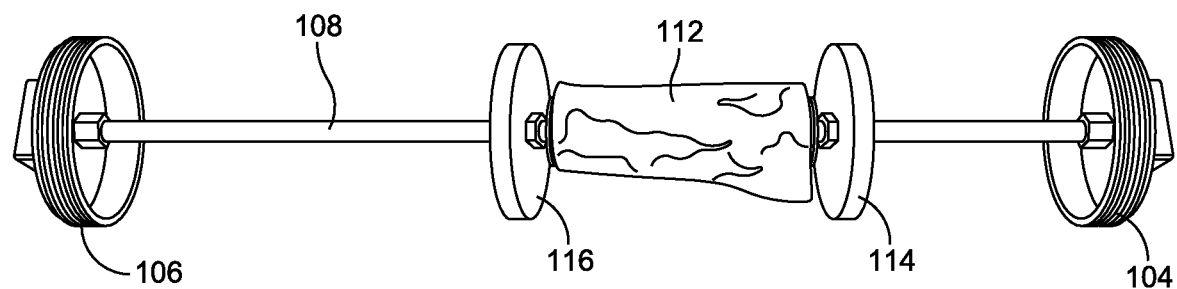
FIGS. 6-7 illustrate an exemplary beef bone disposed about the central shaft of FIG. 6, both before and after tissue debridement using the system of FIGS. 1-4, respectively.
Figure 7:
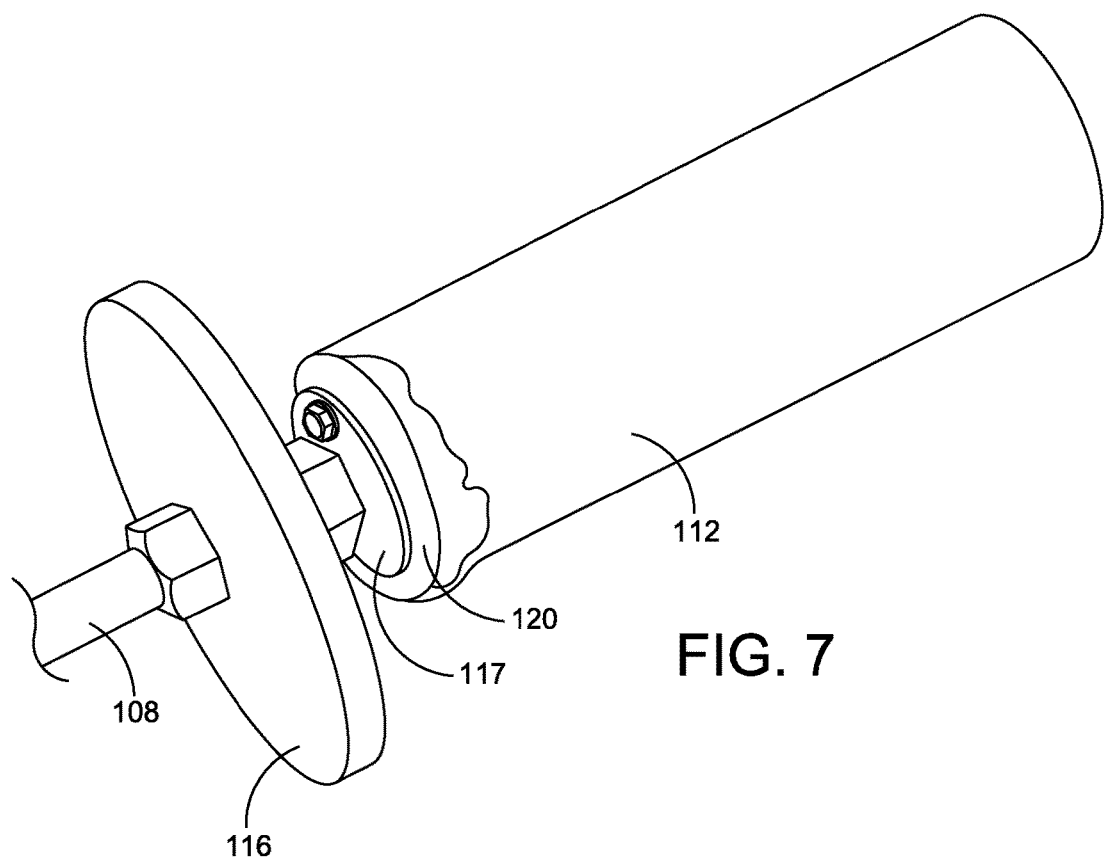

When the water cycle is complete, the cylindrical sleeve 102 may be opened (e.g., by separating the first and the second mating halves 122, 124 of the sleeve 102), and the bone segment 112, now free of extraneous soft tissue, may be removed from the shaft 108 for further processing and ultimate implantation into a patient. FIGS. 6 and 7 show the bone segment 12 (e.g., an exemplary beef bone) before and after debridement, respectively, using the system 100 disclosed herein. The operational debridement time, excluding set-up, is approximately 40 seconds.

Figure 8:
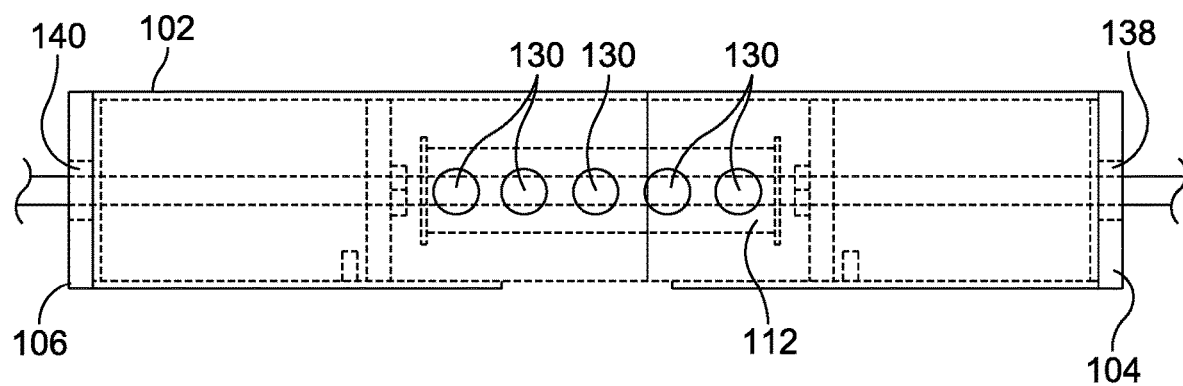
FIGS. 8-9 illustrate side views of one embodiment of the system of FIGS. 1-4, featuring rows of high-pressure water nozzles.
Figure 9:
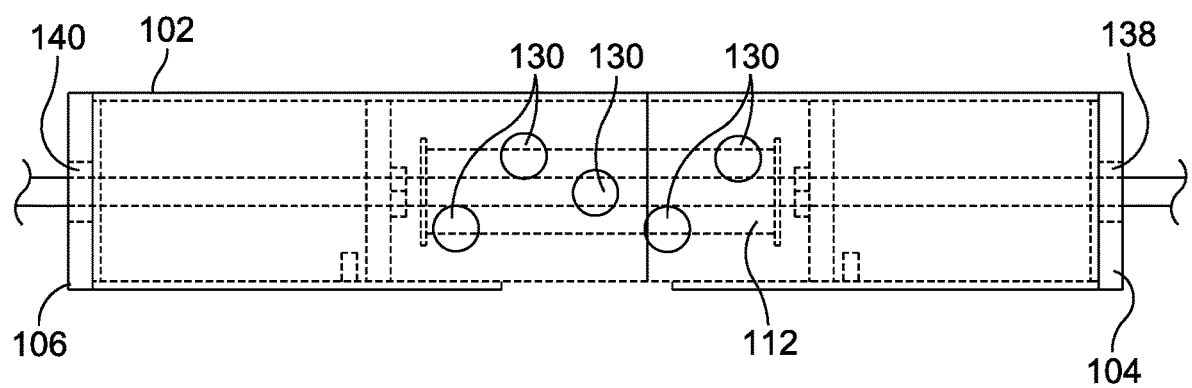

In alternative embodiments shown in FIGS. 8-9, the high-pressure nozzles 130 may be positioned in a row or a set of rows within the sidewall of the cylindrical sleeve 102 in a configuration calculated to cause the hydro impact of the high-pressure water streams to provide the actuating force(s) required to rotate both the shaft 108 and the bone segment 112 relative to the sleeve 102. Thus, the water nozzles 130 may serve as both the actuation and cleansing agents, thereby eliminating the need for the external shaft actuator 115. In these embodiments, the shaft 108 may threadably engage with the nuts 110/endcaps 104, 106, as discussed above, or the shaft 108 may be rotatively coupled with the endcaps 104, 106 via first and second ball bearings 138, 140 disposed within the endcaps 104, 106.

Figure 10:
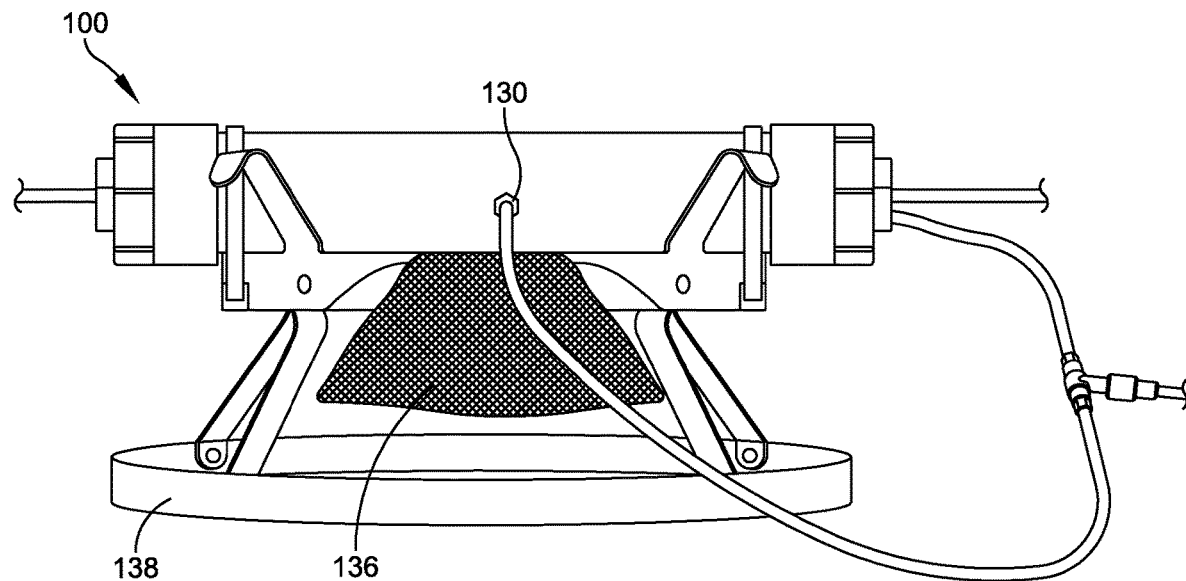
FIGS. 10-11 illustrate side views of the high-pressure water debridement system of FIGS. 1-4 in operation.
Figure 11:
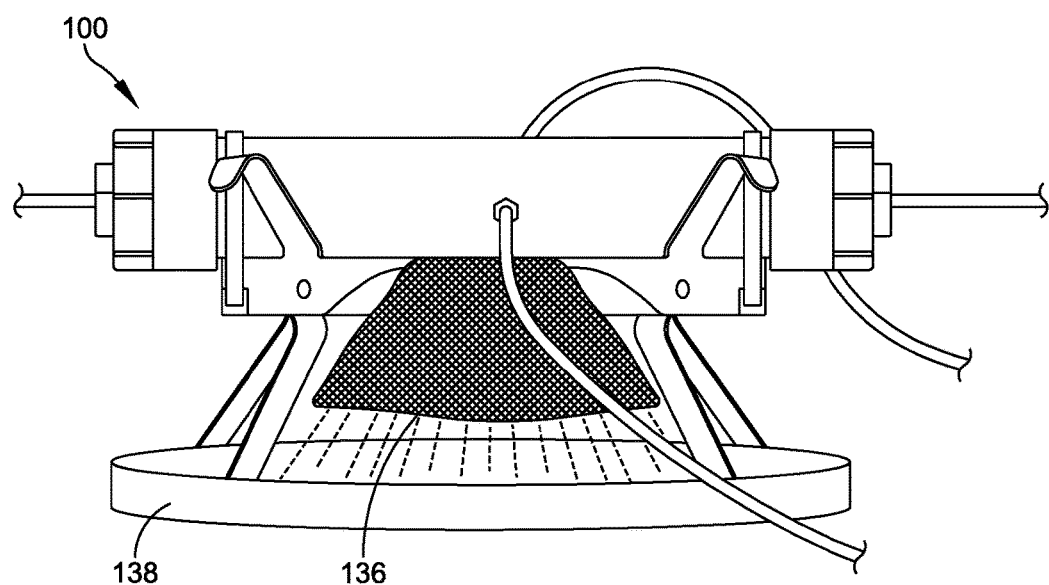

To properly dispose of waste water as well as effluent containing soft tissue debrided from the bone segment 112 during operation, the cylindrical shaft 108 may include a drainage port 134, as shown in FIGS. 1-5. The drainage port 134 may be positioned at any location along or about the cylindrical sleeve 102 to allow for efficient drainage from the sleeve 102 during debridement, as shown in FIGS. 10-11. In operation, the system 100 may be placed over a sink or other receptacle connected to a waste water system. In one embodiment shown in FIGS. 10-11, a porous container such as a mesh bag 136 may be attached to the drainage port 134 to capture effluent solids, while permitting the waste water to pass unimpeded into the waste drain system. If necessary and/or desired, the system 100 may be supported by a support stand or structure 138 having any appropriate size, shape, type, and/or configuration. As a result, the high-pressure water debridement system 100 operates in a manner that is both safe and efficient, and also respectful of the sterile environment within which the debridement procedure takes place.

While the exemplary system 100 depicted in FIGS. 1-5, 8-9, and 10-11 features a horizontal configuration with a downward facing drainage port, it should be understood that the physical configuration of the system may take any appropriate size, shape, type, and/or configuration to achieve automated, high-pressure water debridement that limits or negates manual requirements for both tissue removal and system actuation. For example, the cylindrical sleeve 102 may operate in a vertical configuration, with a drainage port 134 located on a lower portion of the sleeve 102 or within a lower one of the endcaps 104, 106.

System components may be formed of grades 304 and/or 316 stainless steel to render the construction suitable for hydrothermal sterilization by autoclave. Alternatively, the system may be constructed from autoclavable plastics such as high-impact polyvinyl chloride (PVC), polypropylene (PP), polysulfone (PS), polyetheretherketone (PEEK), polymethylpentene (PMP), polycarbonate (PC), PTFE resin, and polymethyl methacrylate (PMMA).

Figure 12:
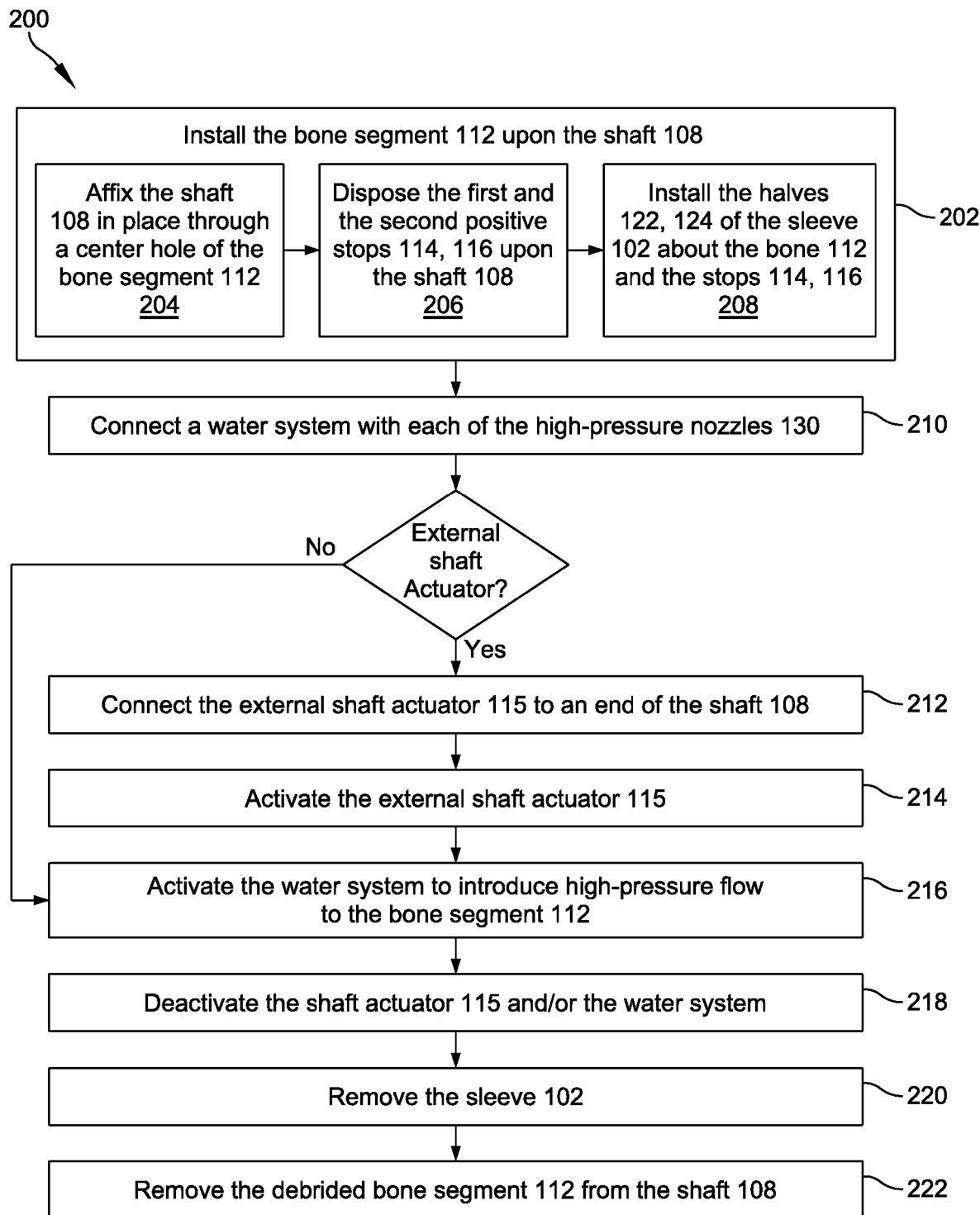
FIG. 12 provides a flowchart depicting an exemplary method of use for the high-pressure water debridement system of FIGS. 1-4.

FIG. 12 provides a flowchart depicting an exemplary method (200) of employing the high-pressure water debridement system 100 to debride soft tissue from a bone segment 112. The method begins with installing the bone segment 112 upon the rotating shaft 108 (202). The installation (202) may involve affixing the shaft 108 in place through a center hole of the bone segment 112 (204), disposing the first and the second positive stops 114, 116 upon the shaft 108 about the first and the second ends 118, 120 of the bone segment 112 (206), and disposing the first and the second mating halves 122, 124 of the cylindrical sleeve 102 about the bone segment 112 and the positive stops 114, 116 (208) such that the bone segment 112 and the positive stops 114, 116 are disposed within the sleeve 102 and between the travel limits 126, 128, and the center shaft 108 protrudes from the sleeve 102 through the first and second endcaps 104, 106.

The method (200) may continue with connecting any appropriate water system with each of the high-pressure nozzles 130 (210). In one embodiment, an end of the shaft 108 may be coupled with the external shaft actuator 115 (212) before the external actuator 115 is activated (214). In another embodiment in which the high-pressure flow from the nozzles 130 serves as the rotational actuator, the water system may simply be activated to introduce high-pressure flow to the bone segment 112 (216). After a debridement period, the water system and, if used, the external shaft actuator 115 may be deactivated (218) before the halves 122, 124 of the sleeve 102 are separated and removed from about the bone segment 112 and the shaft 108 (220), and the debrided bone segment 212 is removed from the shaft (222).

Embodiments of the high-pressure water debridement system 100 and the associated method of use 200 discussed herein provide for safe soft tissue debridement that significantly reduces repetitive arm-hand motions and user exposure to sharp objects. The system is also efficient, cutting the traditional manual debridement time from eight minutes (average) to approximately 40 seconds, and more effective in that embodiments of the high-pressure water debridement system 100 discussed above provide for greater tissue removal than conventional, manual methods.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of debriding soft tissue from a cadaveric bone segment using a high-pressure water debridement system including:
   an outer sleeve defining a longitudinal axis and having an interior bounded by an outer wall, the outer wall bounded at first and second longitudinal ends by respective first and second endcaps;
   a central shaft extending between the first and second endcaps along the longitudinal axis and rotatively coupled between the first and the second endcaps; and
   a plurality of high-pressure water nozzles disposed within the outer wall of the outer sleeve, the method comprising:
   inserting the central shaft through a longitudinal center hole of the bone segment such that the bone segment is disposed about the central shaft and positioned within a spray zone bounded by a first positive stop and a second positive stop;
   disposing the outer sleeve about the bone segment and the first and the second positive stops such that a first end of the central shaft protrudes from the first endcap and a second end of the central shaft protrudes from the second endcap;
   rotating the central shaft relative to the first and the second endcaps such that the bone segment rotates relative to the outer sleeve and oscillates linearly along the longitudinal axis within the spray zone; and
   activating the plurality of the high-pressure water nozzles such that each of the plurality of the high-pressure water nozzles directs a high-pressure water stream into the spray zone, thereby debriding the bone segment.

2. The method of claim 1, wherein the rotating the central shaft comprises activating an external actuator rotatively coupled with an end of the central shaft.

3. The method of claim 1, wherein the rotating the central shaft comprises the activating the plurality of the high-pressure water nozzles.

4. The method of claim 1, the method further comprising capturing, using a porous container attached to a drainage port formed within the outer sleeve, effluent solids debrided from the bone segment.

5. The method of claim 4, wherein the porous container comprises a mesh bag.

6. The method of claim 1, wherein each of the plurality of the high-pressure water nozzles is coupled with a water manifold system.

7. The method of claim 1, wherein the disposing the outer sleeve about the bone segment and the first and the second positive stops comprises:
   disposing a first half of the outer sleeve about the first positive stop and a first portion of the bone segment;
   disposing a second half of the outer sleeve about the second positive stop and a second portion of the bone segment; and
   connecting the first and the second halves to one another.

8. The method of claim 1, wherein:
   the central shaft comprises a threaded shaft;
   the threaded shaft extends through a first threaded nut disposed within the first endcap and a second threaded nut disposed within the second endcap; and
   the rotating the central shaft comprises:
   rotating the threaded shaft in a first direction within the first and the second threaded nuts such that the threaded shaft and the bone segment travel linearly along the longitudinal axis away from the first positive stop toward the second positive stop; and
   rotating the threaded shaft in a second direction within the first and the second threaded nuts such that the threaded shaft and the bone segment travel linearly along the longitudinal axis away from the second positive stop and toward the first positive stop.

9. A method of debriding soft tissue from a cadaveric bone segment, comprising:
   providing a high-pressure water debridement system, including:
   a cylindrical sleeve having an interior bounded at first and second longitudinal ends by respective first and second endcaps;
   a threaded central shaft extending between the first and the second endcaps along a longitudinal axis defined by the cylindrical sleeve, the threaded central shaft rotatively coupled between the first and the second endcaps by first and second threaded nuts disposed within the first and the second endcaps, respectively; and
   opposing high-pressure water nozzles disposed on either side of the cylindrical sleeve;
   inserting the threaded central shaft through a longitudinal center hole of the bone segment such that the bone segment is disposed about the threaded central shaft;
   disposing the cylindrical sleeve about the bone segment such that a first end of the threaded central shaft engages with the first threaded nut and a second end of the threaded central shaft engages with the second threaded nut;
   activating the opposing high-pressure water nozzles such that the opposing high-pressure water nozzles direct a high-pressure water stream toward the bone segment; and
   rotating the threaded central shaft relative to the first and the second threaded nuts such that the bone segment rotates relative to the cylindrical sleeve and oscillates linearly along the longitudinal axis in contact with the high-pressure water stream such that the high-pressure water stream debrides the bone segment.

10. The method of claim 9, further comprising:
    prior to the disposing the cylindrical sleeve about the bone segment, disposing a first positive stop between a first end of the bone segment and the first endcap and a second positive stop between a second end of the bone segment and the second endcap, thereby forming a spray zone between the first and the second positive stops such that the rotating the threaded central shaft causes the bone segment to oscillate linearly along the longitudinal axis within the spray zone.

11. The method of claim 10, wherein the rotating the threaded central shaft comprises:

rotating the threaded central shaft in a first direction within the first and the second threaded nuts such that the threaded central shaft and the bone segment travel linearly along the longitudinal axis away from the first positive stop toward the second positive stop; and rotating the threaded central shaft in a second direction within the first and the second threaded nuts such that the threaded central shaft and the bone segment travel linearly along the longitudinal axis away from the second positive stop and toward the first positive stop.

12. The method of claim 10, wherein the rotating the threaded central shaft comprises:

coupling a rotational actuator to the threaded central shaft; and first activating the rotational actuator to rotate the threaded central shaft in a first direction within the first and the second threaded nuts such that the threaded central shaft and the bone segment travel linearly along the longitudinal axis away from the first positive stop toward the second positive stop; and second activating the rotational actuator to rotate the threaded central shaft in a second direction within the first and the second threaded nuts such that the threaded shaft and the bone segment travel linearly along the longitudinal axis away from the second positive stop and toward the first positive stop.

13. The method of claim 9, further comprising draining effluent from the cylindrical sleeve through an effluent drainage port formed in the cylindrical sleeve.

14. The method of claim 13, further comprising capturing, using a porous receiver attached to the drainage port, effluent solids debrided from the bone segment.

15. The method of claim 9, wherein the rotating the threaded central shaft comprises the activating the opposing high-pressure water nozzles.

16. A method of debriding soft tissue from a cadaveric bone segment, comprising:

providing an outer sleeve having an interior bounded at first and second longitudinal ends by respective first and second endcaps, the outer sleeve defining a longitudinal center axis;

inserting a central shaft through a longitudinal center hole of the bone segment such that the bone segment is disposed about the central shaft;

extending the central shaft between the first and the second endcaps along the longitudinal center axis of the outer sleeve;

disposing one or more high-pressure water nozzles on each side of the outer sleeve in a position configured to impact the bone segment with a high-pressure water steam; and rotating the central shaft relative to the outer sleeve such that the bone segment rotates relative to the outer sleeve and oscillates linearly along the longitudinal center axis in contact with the high-pressure water stream of the one or more high-pressure water nozzles, thereby causing the high-pressure water stream to debride the soft tissue from the bone segment.

17. The method of claim 16, further comprising:

prior to the inserting the central shaft, disposing respective first and second threaded nuts within the first and second endcaps, wherein:

the extending the central shaft between the first and the second endcaps comprises rotationally coupling a threaded central shaft between the first and the second threaded nuts; and the rotating the central shaft relative to the outer sleeve comprises rotating the threaded central shaft within the first and the second threaded nuts.

18. The method of claim 17, wherein the extending the central shaft between the first and the second endcaps further comprises:

disposing a first positive stop between a first end of the bone segment and the first endcap and a second positive stop between a second end of the bone segment and the second endcap, thereby forming a spray zone between the first and the second positive stops such that the rotating the threaded central shaft within the first and second threaded nuts causes the bone segment to oscillate linearly along the longitudinal axis within the spray zone.

19. The method of claim 18, wherein the rotating the threaded central shaft within the first and the second threaded nuts comprises:

rotating the threaded central shaft in a first direction within the first and the second threaded nuts such that the threaded central shaft and the bone segment travel linearly along the longitudinal axis away from the first positive stop toward the second positive stop; and rotating the threaded central shaft in a second direction within the first and the second threaded nuts such that the threaded central shaft and the bone segment travel linearly along the longitudinal axis away from the second positive stop and toward the first positive stop.

20. The method of claim 16, further comprising:

capturing, using a porous container attached to a drainage port formed within the outer sleeve, effluent solids debrided from the bone segment.

\* \* \* \* \*